(12) United States Patent
Chan et al.

(10) Patent No.: US 11,874,530 B2
(45) Date of Patent: Jan. 16, 2024

(54) HEAD-MOUNTED DISPLAY DEVICE WITH VISION CORRECTION

(71) Applicant: Apple Inc., Cupertino, CA (US)

(72) Inventors: Victoria C. Chan, Sunnyvale, CA (US); Christina G. Gambacorta, Sunnyvale, CA (US); Graham B. Myhre, San Jose, CA (US); Hyungryul Choi, San Jose, CA (US); Nan Zhu, San Jose, CA (US); Phil M. Hobson, Menlo Park, CA (US); William W. Sprague, Berkeley, CA (US); Edward A. Valko, San Jose, CA (US); Qiong Huang, San Jose, CA (US); Branko Petljanski, San Jose, CA (US); Paul V. Johnson, San Francisco, CA (US); Brandon E. Clarke, Sunnyvale, CA (US); Elijah H. Kleeman, San Jose, CA (US)

(73) Assignee: Apple Inc., Cupertino, CA (US)

( * ) Notice: Subject to any disclaimer, the term of this patent is extended or adjusted under 35 U.S.C. 154(b) by 522 days.

(21) Appl. No.: 16/612,336

(22) PCT Filed: May 3, 2018

(86) PCT No.: PCT/US2018/030832
§ 371 (c)(1),
(2) Date: Nov. 8, 2019

(87) PCT Pub. No.: WO2018/213010
PCT Pub. Date: Nov. 22, 2018

(65) Prior Publication Data
US 2020/0174284 A1 Jun. 4, 2020

Related U.S. Application Data

(60) Provisional application No. 62/507,671, filed on May 17, 2017.

(51) Int. Cl.
*G02C 7/08* (2006.01)
*A61B 3/00* (2006.01)
(Continued)

(52) U.S. Cl.
CPC ............ *G02C 7/083* (2013.01); *A61B 3/0008* (2013.01); *A61B 3/032* (2013.01); *A61B 3/036* (2013.01);
(Continued)

(58) Field of Classification Search
CPC ...... G02C 7/083; G02C 2202/22; G02C 7/02; A61B 3/0008; A61B 3/032; A61B 3/036;
(Continued)

(56) References Cited

U.S. PATENT DOCUMENTS 8,384,999 B1 2/2013 Crosby et al.
8,488,246 B2 7/2013 Border et al.
(Continued)

FOREIGN PATENT DOCUMENTS

CN 103365028 A 10/2013
CN 106249412 A 12/2016
(Continued)

*Primary Examiner* — Cara E Rakowski
(74) *Attorney, Agent, or Firm* — Treyz Law Group, P.C.; G. Victor Treyz; Tianyi He (57) ABSTRACT

A head-mounted display may include a display system and an optical system in a housing. The display system may have displays that produce images. Positioners may be used to move the displays relative to the eye positions of a user's eyes. An adjustable optical system may include tunable lenses such as tunable cylindrical liquid crystal lenses. The displays may be viewed through the lenses when the user's eyes are at the eye positions. A sensor may be incorporated into the head-mounted display to measure refractive errors in the user's eyes. The sensor may include waveguides and volume holograms, and a camera for gathering light that has (Continued)

reflected from the retinas of the user's eyes. Viewing comfort may be enhanced by adjusting display positions relative to the eye positions and/or by adjusting lens settings based on the content being presented on the display and/or measured refractive errors.

26 Claims, 9 Drawing Sheets

(51) Int. Cl.
| | | |
|---|---|---|
| *A61B 3/032* | (2006.01) | |
| *A61B 3/036* | (2006.01) | |
| *G02B 6/42* | (2006.01) | |
| *G02B 7/02* | (2021.01) | |
| *G02B 7/09* | (2021.01) | |
| *G02F 1/133* | (2006.01) | |
| *G06F 1/16* | (2006.01) | |
| *G02F 1/1343* | (2006.01) | |

(52) U.S. Cl.
CPC .......... *G02B 6/4204* (2013.01); *G02B 7/023* (2013.01); *G02B 7/09* (2013.01); *G02F 1/13306* (2013.01); *G06F 1/163* (2013.01); *G02F 1/13439* (2013.01)

(58) Field of Classification Search
CPC ... A61B 1/0692; A61B 3/1015; A61B 3/0025; A61B 3/0033; A61B 3/0041; G02B 6/4204; G02B 7/023; G02B 7/09; G02B 27/0172; G02B 2027/0138; G02B 27/0179; G02B 3/14; G02B 2027/0159; G02B 2027/0161; G02B 2027/0163; G02B 2027/0178; G02B 2027/0187; G02F 1/13306; G02F 1/13439; G06F 1/163; H04N 5/7491
USPC ...... 359/13–14, 629–633; 345/7–9; 348/115; 349/11; 351/41–159, 178, 206, 211–212
See application file for complete search history.

(56) References Cited

U.S. PATENT DOCUMENTS

| | | | |
|---|---|---|---|
| 9,292,973 | B2 | 3/2016 | Bar-Zeev et al. |
| 9,492,074 | B1 | 11/2016 | Lee et al. |
| 9,684,172 | B2 | 6/2017 | Border et al. |
| 2007/0097277 | A1 | 5/2007 | Hong et al. |
| 2012/0105486 | A1 | 5/2012 | Lankford et al. |
| 2012/0127062 | A1 | 5/2012 | Bar-Zeev et al. |
| 2013/0182224 | A1 | 7/2013 | Schweigerling et al. |
| 2014/0266990 | A1* | 9/2014 | Makino .............. G02B 27/0172 345/8 |
| 2014/0375542 | A1 | 12/2014 | Robbins et al. |
| 2015/0185475 | A1 | 7/2015 | Saarikko et al. |
| 2015/0234206 | A1* | 8/2015 | Lee ........................ G02C 7/083 351/206 |
| 2016/0109712 | A1* | 4/2016 | Harrison ................ G02B 27/30 345/8 |
| 2016/0270656 | A1* | 9/2016 | Samec .................. A61B 3/0008 |
| 2017/0000335 | A1 | 1/2017 | Samec et al. |
| 2017/0045741 | A1 | 2/2017 | Raffle et al. |
| 2018/0263488 | A1* | 9/2018 | Pamplona ............ A61B 3/0041 |
| 2018/0321426 | A1* | 11/2018 | Weinstock ............... G02B 3/08 |

FOREIGN PATENT DOCUMENTS

| | | |
|---|---|---|
| CN | 106444028 A | 2/2017 |
| JP | H02149916 U | 12/1990 |
| JP | H08286144 A | 11/1996 |
| JP | H08292394 A | 11/1996 |
| JP | 2003505718 A | 2/2003 |
| JP | 2005122026 A | 5/2005 |
| JP | 2010204397 A | 9/2010 |
| JP | 2011507011 A | 3/2011 |
| JP | 2014071230 A | 4/2014 |
| JP | 2015521926 A | 8/2015 |
| JP | 2016148839 A | 8/2016 |
| JP | 2017037235 A | 2/2017 |
| KR | 20130127472 A | 11/2013 |
| KR | 20150093169 A | 8/2015 |
| KR | 20160048800 A | 5/2016 |
| KR | 20160102481 A | 8/2016 |
| WO | 2009041055 A1 | 4/2009 |
| WO | 2015012280 A1 | 1/2015 |
| WO | 2017071458 A1 | 5/2017 |

\* cited by examiner

HEAD-MOUNTED DISPLAY DEVICE WITH VISION CORRECTION

This application claims priority to provisional patent application No. 62/507,671, filed May 17, 2017, which is hereby incorporated by reference herein in its entirety.

BACKGROUND

This relates generally to optical systems and, more particularly, to optical systems for head-mounted devices.

Head-mounted devices such as virtual reality glasses and augmented reality glasses use displays to generate images and use lenses to present the images to the eyes of a user.

If care is not taken, a head-mounted device may be cumbersome and tiring to wear. Optical systems for head-mounted devices may be bulky and heavy and may not be sufficiently adjustable. Extended use of a head-mounted device with this type of optical system may be uncomfortable.

SUMMARY

A head-mounted display device may include a display system and an optical system in a housing. The display system may have displays that produce images. Positioners may be used to move the displays relative to a user's eyes. The positioners may be used to adjust the horizontal separation of the displays from each other to accommodate differences in interpupillary distance between users, may be used to make vertical display location adjustments to accommodate differences in facial anatomy between users, and may be used in adjusting eye-to-display spacing to alter focus.

The optical system may include tunable lenses such as tunable cylindrical liquid crystal lenses. The displays may be viewed through the lenses. The optical system may include fixed spherical lenses that are used in conjunction with the tunable cylindrical lenses.

A sensor may be incorporated into the head-mounted device to measure refractive errors in the user's eyes. Viewing comfort may be enhanced by adjusting display position relative to the eye positions of the user's eyes and/or by adjusting lens settings based on the content being presented on the display and/or based on measured eye refractive errors. The sensor may include waveguides and volume holograms and a camera for gathering light that has reflected from the retinas of the user's eyes. Refractive errors such as farsightedness, nearsightedness, and astigmatism may be corrected by tuning the lenses and/or adjusting display positions.

DETAILED DESCRIPTION

Head-mounted devices such as head-mounted displays may be used for virtual reality and augmented reality systems. For example, a pair of virtual reality glasses that is worn on the head of a user may be used to provide a user with virtual reality content.

Figure 1:
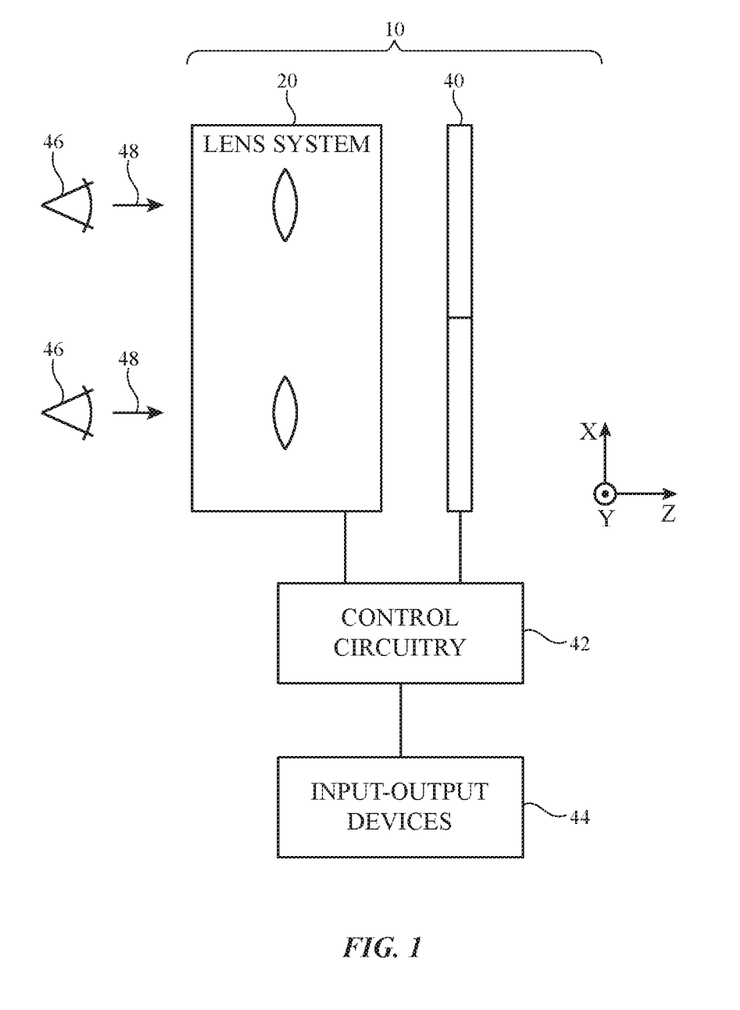
FIG. 1 is a diagram of an illustrative head-mounted device in accordance with an embodiment.

An illustrative system in which a head-mounted device such as a pair of virtual reality glasses is used in providing a user with virtual reality content is shown in FIG. 1. As shown in FIG. 1, head-mounted display 10 may include a display system such as display system 40 that creates images and may have an optical system such as optical system 20 through which a user (see, e.g., user's eyes 46) may view the images produced by display system 40 in direction 48.

Display system 40 may be based on a liquid crystal display, an organic light-emitting diode display, a display having an array of crystalline semiconductor light-emitting diode dies, a liquid-crystal-on-silicon display, a microelectromechanical systems (MEMs) display, and/or displays based on other display technologies. Separate left and right displays may be included in system 40 for the user's left and right eyes or a single display may span both eyes.

Visual content (e.g., image data for still and/or moving images) may be provided to display system 40 using control circuitry 42 that is mounted in head-mounted device 10 and/or control circuitry that is mounted outside of head-mounted device 10 (e.g., in an associated portable electronic device, laptop computer, or other computing equipment). Control circuitry 42 may include storage such as hard-disk storage, volatile and non-volatile memory, electrically programmable storage for forming a solid-state drive, and other memory. Control circuitry 42 may also include one or more microprocessors, microcontrollers, digital signal processors, graphics processors, baseband processors, application-specific integrated circuits, and other processing circuitry. Communications circuits in circuitry 42 may be used to transmit and receive data (e.g., wirelessly and/or over wired paths). Control circuitry 42 may use display system 40 to display visual content such as virtual reality content (e.g., computer-generated content associated with a virtual world), pre-recorded video for a movie or other media, or other images.

System 40 may include electrically controlled positioners that can be used to adjust the positions of the displays in system 40. Lens system 20 may include tunable lenses. During operation, control circuitry 42 may make position adjustments to the displays in system 40, may adjust the tunable lenses in lens system 20, and/or may make other adjustments to the components of device 10 while using system 40 to present the user with image content.

Input-output devices 44 may be coupled to control circuitry 42. Input-output devices 44 may be used to gather user input from a user, may be used to make measurements on the environment surrounding device 10, may be used to provide output to a user, and/or may be used to supply output to external electronic equipment. Input-output devices 44 may include buttons, joysticks, keypads, keyboard keys, touch sensors, track pads, displays, touch screen displays, microphones, speakers, light-emitting diodes for providing a user with visual output, and sensors (e.g., force sensors, temperature sensors, magnetic sensor, accelerometers, gyroscopes, and/or other sensors for measuring orientation, position, and/or movement of glasses 10, proximity sensors, capacitive touch sensors, strain gauges, gas sensors, pressure sensors, ambient light sensors, and/or other sensors). If desired, input-output devices 44 may include a sensing system that measures the eye characteristics of the user's eyes 46. For example, a wavefront sensor such as a Shack-Hartmann wavefront sensor, Tscherning sensor, or a ray tracing sensor may be used to measure refractive errors in a user's eyes such as astigmatism, farsightedness, and near-sightedness. Devices 44 can also include cameras (digital image sensors) for capturing images of the user's surroundings, cameras for performing gaze detection operations by viewing eyes 46, and/or other cameras.

Figure 2:
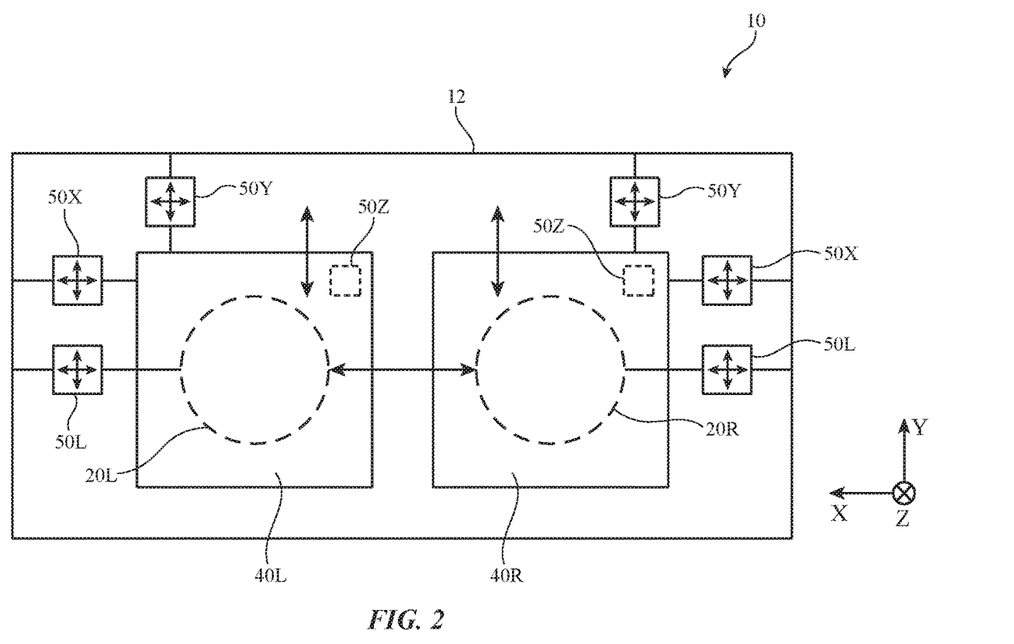
FIG. 2 is a diagram of an illustrative head mounted device with adjustable displays and lenses in accordance with an embodiment.

FIG. 2 is a diagram of portions of head-mounted device 10 viewed in direction 48 of FIG. 1 (along the Z axis in FIG. 2). As shown in FIG. 2, optical system components such as left lens 20L and right lens 20R and display system components such as left display 40L and right display 40R for device 10 may be mounted in a housing such as housing 12. Housing 12 may have the shape of a frame for a pair of glasses (e.g., head-mounted device 10 may resemble eyeglasses), may have the shape of a helmet (e.g., head-mounted device 10 may form a helmet-mounted display), may have the shape of a pair of goggles, or may have any other suitable housing shape that allows housing 12 to be worn on the head of a user. Configurations in which housing 12 supports optical system 20 and display system 40 in front of a user's eyes (e.g., eyes 46) as the user is viewing optical system 20 and display system 40 in direction 48 may sometimes be described herein as an example. If desired, housing 12 may have other suitable configuration.

Housing 12 may be formed from plastic, metal, fiber-composite materials such as carbon-fiber materials, wood and other natural materials, glass, other materials, and/or combinations of two or more of these materials. Electrically controlled positioners (e.g., computer-controlled stepper motors, piezoelectric actuators, or other computer-controlled positioning devices that are controlled by control signals from control circuitry 42) can be coupled to components of device 10 and used in positioning these components in desired positions relative to housing 12 and relative to the user wearing device 10. For example, positioners 50X may be used to adjust the respective X-axis positions of displays 40L and 40R. Positioners 50Y may be used to adjust the respective positions of displays 40L and 40R along the Y-axis of FIG. 2. The Z-axis positions of displays 40L and 40R (respectively, the distances of displays 40L and 40R to the user's left and right eyes 46) may be adjusted using positioners 50Z. Positioners 50L (e.g., X-axis, Y-axis, Z-axis, and/or rotational positioners) may be used in adjusting the positions of lenses 20L and 20R. Lens properties can also be electrically tuned in response to control signals from control circuitry 42. The positioners in device 10 may be coupled to housing 12 (e.g., to move the position of a component relative to housing 12) and/or may be coupled to movable structures in device 10 (e.g., to adjust the position of one component relative to another component or relative to a movable support structure). If desired, lens 20L may be coupled to display 40L using fixed support structures and lens 20R may be coupled to display 40R using fixed support structures so that the displays and corresponding lenses move together. In other configurations, the positions of lenses 20L and 20R can be fixed (or adjustable) with respect to the user's eyes while the positions of displays 40L and 40R relative to the user's eyes can be independently adjusted using the positioners for displays 40L and 40R. In some arrangements, lens positioners 50L may be omitted. Arrangements in which lens positioners only provide rotational positioning for lenses 20L and 20R may also be used.

The adjustability of the positions of displays 40L and 40R and/or of lenses 20L and 20R along the Z-axis allows images on displays 40L and 40R to be brought into focus for the user. Inward and outward position adjustments parallel to the X-axis allow device 10 to accommodate users with different interpupillary distances; each lens and panel pair (corresponding to one eye) must be adjusted together. Adjustments along the Y dimension may allow device 10 to accommodate differences in user head and face anatomy (e.g., to place the displays and lenses at different heights along axis Y relative to the user's eyes). Positioner operations may be controlled in response to user input. For example, control circuitry 42 can use the positioners of FIG. 2 to make position adjustments based on button press input, touch sensor input, voice input, on-screen menu selections, and/or other user input to devices 44 of FIG. 1. Position adjustments (e.g., for focus tuning) can also be made by control circuitry 42 automatically based on measured refractive characteristics of the eyes of a user.

Figure 3:
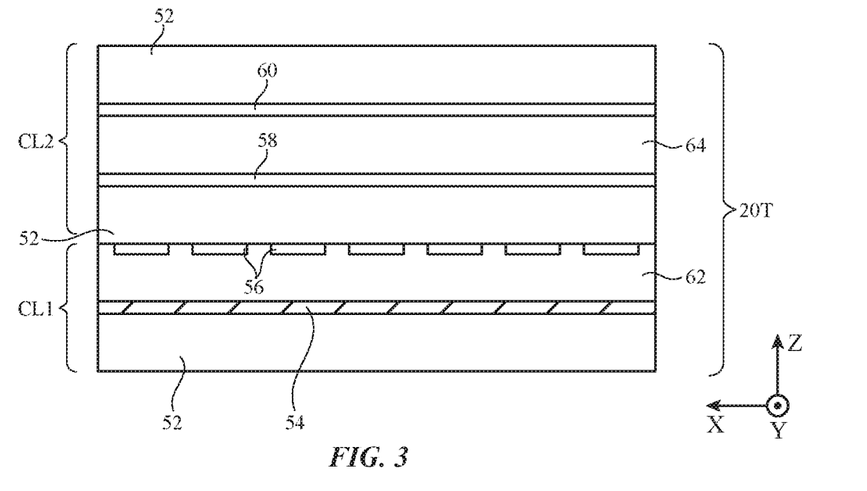
FIG. 3 is a cross-sectional side view of an illustrative adjustable lens in accordance with an embodiment.

In addition to using lens movement and/or display movement to perform focusing operations, lenses 20L and 20R may be electrically tuned based on control signals from control circuitry 42. Lenses 20L and 20R may be, for example, tunable lenses such as tunable liquid crystal lenses or other lenses that can be dynamically tuned to exhibit different focal lengths. In the example of FIG. 3, tunable lens 20T (e.g., lens 20L and/or lens 20R) has been formed from a pair of orthogonally oriented stacked tunable cylindrical lenses. In particular, tunable lens 20T has a first tunable cylindrical lens CL1 and a second tunable lens CL2 formed from liquid crystal lens structures. Polarizers (e.g., linear polarizers with aligned pass axes) may be placed above CL2 and below CL1.

Lens 20T may include substrates such as substrates 52. Substrates 52 may be formed from clear plastic, transparent glass, or other suitable transparent material. Transparent conductive electrodes such as electrodes 54, 56, 58, and 60 may be formed on substrates 52. The transparent conductive electrodes may be formed from indium tin oxide or other transparent conductive material. Photolithography and etching, shadow mask patterning, or other patterning techniques may be used in patterning the electrodes into desired shapes (e.g., rings, strips, pads in an array, etc.).

With one illustrative configuration, which is shown in FIG. 3, lower electrode 54 of tunable cylindrical lens CL1 is formed from a blanket layer of transparent conductive material and upper electrode 56 of tunable cylindrical lens CL1 is formed from patterned strips of transparent conductive material running parallel to the Y axis. Liquid crystal material 62 is interposed between electrode 54 and electrode 56. The index of refraction of liquid crystal material varies as a function of applied voltage (electric field through the liquid crystal). By independently adjusting the voltages on each of electrodes 56 across dimension X, the index of refraction of liquid crystal material 62 can be adjusted under each electrode 56 and the focal length of cylindrical lens CL1 can therefore be adjusted.

Because electrodes 56 run along the Y axis of FIG. 3, the elongated axis of cylindrical lens CL1 also runs parallel to the Y axis. In upper tunable cylindrical lens CL2, liquid crystal material 64 is interposed between electrode 60 and electrode 58. Electrode 58 may be a uniform layer of transparent conductive material and upper electrode 60 may be formed from patterned strips of transparent conductive material running parallel to the X-axis. By adjusting the voltages applied to the electrode strips of electrode 60, the focal length of tunable cylindrical lens CL2 may be adjusted. The electrode strips of electrode 60 extend along the X-axis, so the longitudinal axis of lens CL2 also extends along the X axis. Because lenses CL1 and CL2 are perpendicular to each other, selected cylindrical lens powers in orthogonal directions may be produced through tuning of lenses CL1 and CL2. Spherical lens powers may be produced by driving both CL1 and CL2 (electrodes in X and Y) parametrically.

Figure 4:
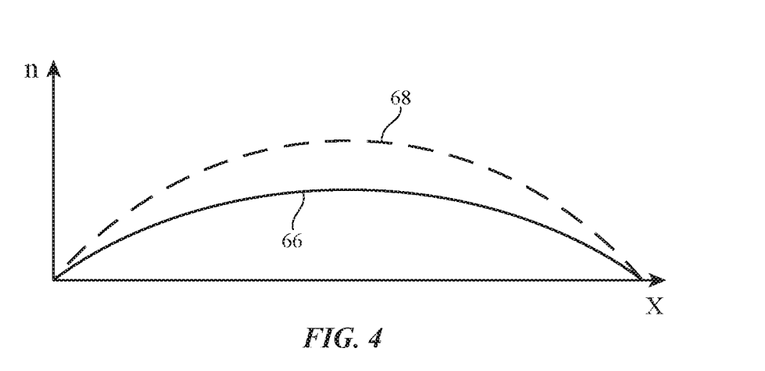
FIG. 4 is a graph showing how the index of refraction of the lens of FIG. 3 may be adjusted in accordance with an embodiment.

FIG. 4 is a graph showing how the focal length of a tunable cylindrical lens (e.g., the focal length of CL1) can be adjusted. In a first configuration, a smoothly varying profile of voltages is applied to across the electrode strips of the tunable cylindrical lens, causing the index-of-refraction n for the lens to be characterized by refractive index profile 66 of FIG. 4. The value of refractive index n varies in a curved shape across dimension X, thereby creating a cylindrical lens from the liquid crystal material.

Figure 5:
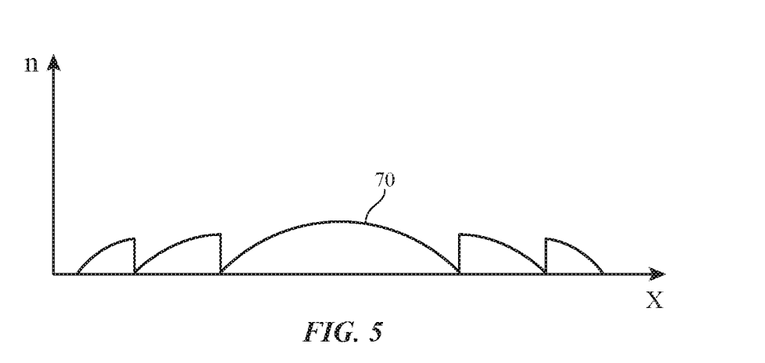
FIG. 5 is a diagram showing how the index of refraction of the lens of FIG. 3 may be adjusted when forming a Fresnel lens in accordance with an embodiment.

To tune the lens, another smoothly varying voltage profile (e.g., with a larger magnitude) may be applied to the liquid crystal material, thereby creating refractive index profile 68. As these examples demonstrate, the refractive index profile of a tunable cylindrical lens can be adjusted dynamically to adjust the focal length of the lens (e.g., to have a longer focal length and weaker lens power as illustrated by profile 66 or to have a shorter focal length and stronger lens power as illustrated by profile 68). If desired, index-of-refraction profiles of the type shown by tunable cylindrical lens index profile 70 of FIG. 5 may be dynamically produced to implement a cylindrical lens of a desired power using a Fresnel lens configuration.

In a tunable lens configuration of the type shown by lens 20T, the longitudinal axes of lenses CL1 and CL2 are orthogonal, allowing a cylindrical lens to be dynamically produced along either the X or Y axis. To help correct the vision of a user with astigmatism, cylindrical lens power along the X and/or Y dimensions can be controlled using lenses CL1 and CL2 of tunable lens 20T. If desired, a tunable cylindrical lens may be rotated using a positioner. For example, lens system 20 may include a mechanically or electrically rotatable cylindrical tunable lens of varying power (e.g., to compensate for eye astigmatism that is not symmetrical about the X or Y axis). Configurations in which the angular orientation of lens 20T is fixed and electrical tuning is used to tune lens CL1 and/or lens CL2 are described herein as an example.

Lens system 20 may include a fixed (or tunable) spherical lens in alignment with lens 20L and a fixed (or tunable) spherical lens in alignment with lens 20R. When a spherical lens is combined with a tunable cylindrical lens, device 10 may adjust tunable lenses in system 20 to correct the vision of a user's eye using a spherical equivalent (e.g., a combination of a spherical lens and a cylindrical lens of appropriate powers to approximate a desired aspherical lens for correcting a user's astigmatism).

If desired, a sensor that is configured to operate as an aberrometer (e.g., a Shack-Hartmann, Tscherning, or ray tracing sensor or other suitable refractive error measurement equipment) may be used by control circuitry 42 to automatically measure refractive errors in the user's eyes. Holographic couplers, waveguides, and other structures of the type shown in FIG. 6A may be used in forming the wavefront sensor so that the wavefront sensor can be reduced in size sufficiently to be carried in head mounted device 10.

Figures 6A, 6B, 6C, 6D:
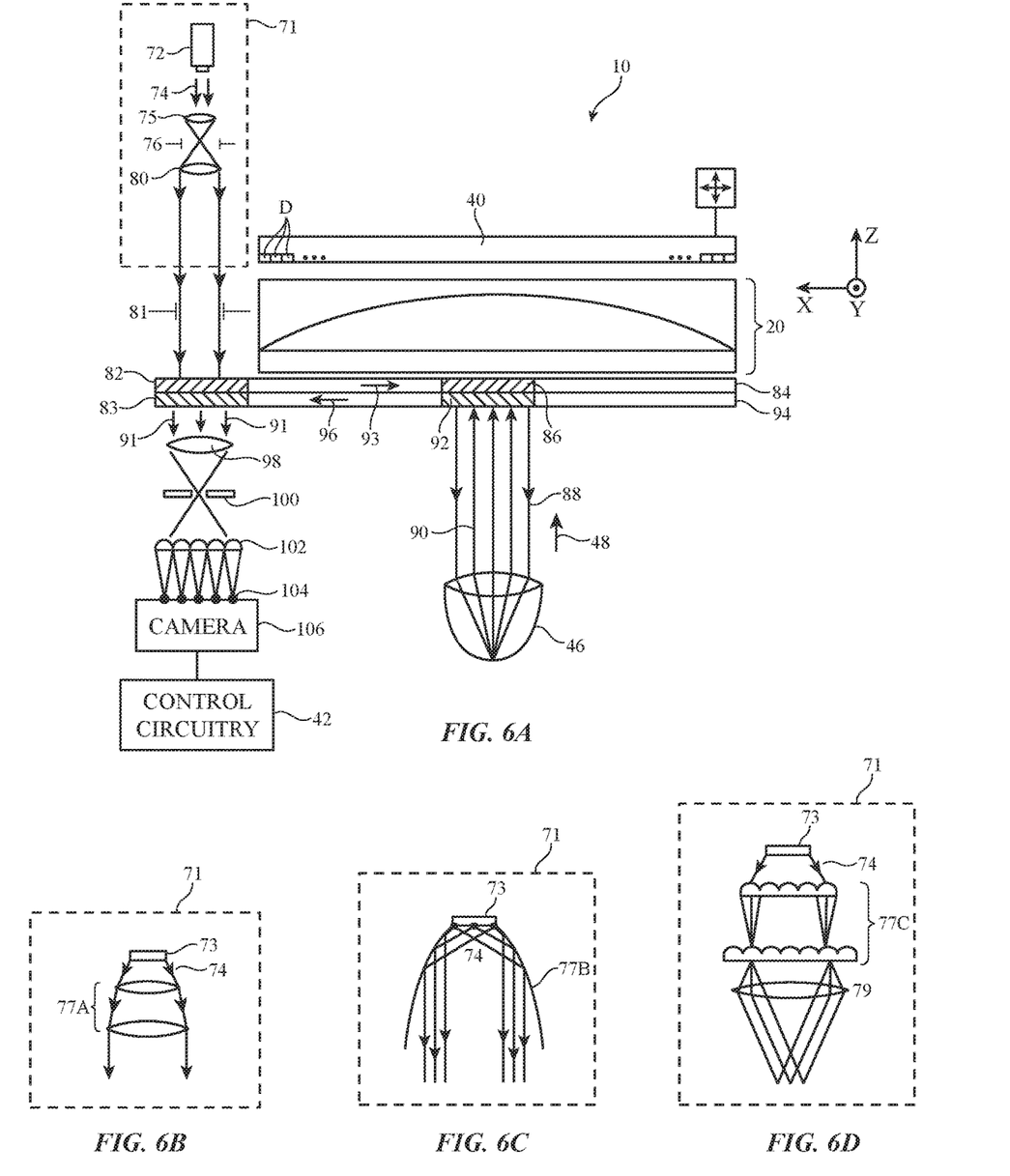
FIG. 6A is a diagram of an illustrative Shack-Hartmann sensor for a head-mounted device in accordance with an embodiment.
FIGS. 6B, 6C, and 6D are diagrams of alternative light sources for the Shack-Hartmann sensor in accordance with embodiments.

Device 10 may include displays such as illustrative display 40 of FIG. 6A. Each display 40 may have an array of pixels P for generating images. As described in connection with FIG. 2, device 10 may have two displays (e.g., displays 40L and 40R) for providing images for the user's left and right eyes 46, respectively. Only one eye 46 and one corresponding display 40 are shown in the example of FIG. 6A.

Position sensors of the type shown in FIG. 2 may be used in adjusting the position of display 40 relative to eye 46 so that the images are in focus and can be comfortably viewed by the user. For example, the separation between display 40 and eye 46 can be adjusted using a Z-axis positioner (as an example). Lens system 20 may include fixed and/or tunable lenses (e.g., a fixed and/or tunable spherical lens, tunable cylindrical lenses, etc.).

In a Shack-Hartmann sensor configuration of the type shown in FIG. 6A, light source 72 and camera 106 may be used in supplying light to eye 46 and measuring reflected light to measure the optical properties of eye 46. Light source 72 may produce light 74 at any suitable wavelength. For example, light source 72 may be an infrared light source such as a laser or light-emitting diode that produces near infrared light (e.g., light at 750-1400 nm, light with a wavelength of at least 700 nm, light with a wavelength of at least 750 nm, light with a wavelength of at least 800 nm, light with a wavelength of less than 1500 nm, light with a wavelength of less than 1000 nm, light with a wavelength of less than 900 nm, or light with a wavelength of less than 850 nm, etc.). Other wavelengths of light (longer infrared wavelengths, visible wavelengths, etc.) can also be used if desired.

For a light source such as a laser, objective lens 75, pinhole aperture 76, collimating lens 80, and iris 81 may be used to collimate and control the beam size of light 74. These optical elements make up collimation optics assembly 71. Objective lens 75 focuses light 74 onto pinhole aperture 76, which acts as a spatial filter that removes uneven intensity distributions in the beam. A beam with a smooth Gaussian profile emerges from pinhole aperture 76. Lens 80 may be used to collect and collimate the spatially filtered light. Iris 81 may be used to control the collimated beam size. The lenses and apertures in assembly 71 may be fixed components, or may be be adjusted either manually or electronically in response to control signals from control circuitry 42.

Light source 72 may be a light-emitting diode (LED) 73 that emits at any suitable wavelength. Because of the finite size of the LED, the beam will diverge slightly after collimation. For an LED source, collimation optics assembly 71 may contain different components to mitigate beam divergence after collimation. FIG. 6B shows a configuration an aspheric lens pair 77A collimates the light 74 from LED source 73. If desired, a single aspheric lens can be used for collimation instead. In FIG. 6C, collimation optics assembly 71 may contain just an LED 73 and compound parabolic concentrator 77B. By sitting at the focus of the hollow parabolic mirror 77B, light 74 can be collected and collimated. Parabolic concentrator 77B is advantageous in cases where the LED source 73 carries a large emission profile that cannot fully be captured by a simple lens. In FIG. 6D, assembly 71 may contain a lens array pair 77C and condenser lens 79. The combination of two lens arrays produces uniform illumination whose beam size can be controlled by condenser lens 79. If desired, a single lens array may be used instead.

Input and output couplers such as volume holograms or other holographic couplers may be used in coupling light into and out of the ends of waveguides 84 and 94. The couplers are directional, meaning that light can enter the volume hologram in one direction. For example, input coupler 82 may be used to couple light 74 into waveguide 84. Once coupled into waveguide 84, this light may travel to output coupler 86 in direction 93 within waveguide 84. Output coupler 86 may be aligned with user's eye 46 (e.g., output coupler 86 may be interposed between display 40 (and lens 20) and the user's eye 46). With this configuration, output coupler 86 couples light that is traveling in direction 93 in waveguide 84 out of waveguide 84 and towards eye 46 as indicated by output light 88. This illuminates the user's eye with light 74. After passing through the lens of eye 46, light 88 is reflected in direction 48, as indicated by reflected light 90. Input coupler 92 couples light 90 into waveguide 94. Couplers 86 and 92 may be tuned to the wavelength of light 74 and may therefore be transparent to the user as the user is viewing images on display 40 in direction 48.

In waveguide 94, light collected from input coupler 92 travels to output coupler 83 in direction 96. Output coupler 83 couples the light exiting waveguide 94 that is traveling in direction 96 towards camera 106 as output light 91. Output light 91 passes through lens 98, low pass filter 100 (which is located at the focus of lens 98 and is used to filter out noise from the light), and lenslet array 102. Lenslet array 102 may include a two-dimensional array of lenses. These lenses focus light 91 onto camera 106 (e.g., a digital image sensor) in a two-dimensional array of spots 104.

The individual intensities of the spots in the two-dimensional pattern of spots 104 at camera 106 can be analyzed by control circuitry 42 to characterize any refractive errors present in user's eye 46 (e.g., astigmatism, nearsightedness, or farsightedness). With one illustrative arrangement, control circuitry 42 fits Zernike polynomials to the measured intensities of spots 104 and processes the Zernike polynomials to determine the user's eye refractive errors (e.g., a diopter value or other eyeglasses prescription information specifying optical system settings to correct the user's vision by correcting refractive errors associated with eye 46). The information on the measured refractive errors can then be used by control circuitry 42 to adjust the position of display 40 relative to eye 46 and/or to adjust one or more tunable lenses in optical system 20.

Consider, as an example, a nearsighted user with astigmatism having a right eye (OD) prescription of sphere: −3.00 diopters, cylinder: −1.50 diopters, axis: 180°. This prescription indicates that the user needs spherical and cylindrical corrections of −3.00 and −1.5 diopters, respectively. The axis value of 180° indicates the user's astigmatism correction is horizontal. In this scenario, the spherical correction can be obtained by adjusting the separation between display 40 and eye 46 with the Z-axis positioner and the cylindrical correction can be obtained by tuning the horizontally oriented tunable cylindrical lens to produce −1.5 diopters of cylindrical lens power. The user's right eye refractive errors can be independently corrected by control circuitry 42 based on the measured characteristics of the user's right eye.

The content that is provided to the user may contain distant images (e.g., images of mountains) and may contain foreground content (e.g., an image of a person standing 50 cm from the user). Three-dimensional content can be provided by presenting slightly different images to the user's left and right eyes with respective displays 40L and 40R.

Accommodation-vergence mismatch has the potential to lead to eyestrain. To minimize eyestrain, device 10 may perform operations that help allow the use's ciliary muscles to relax. For example, control circuitry 42 may periodically (e.g., every 20 minutes) present distant content (e.g., content at an apparent distance of at least 20 feet away) to the user and may direct the user to look at this distant content for a predetermined amount of time (e.g., 20 seconds). Adjustments can also be made to the diopter correction or other optical system settings associated with device 10 to help enhance user eye comfort. For example, device 10 can be calibrated during manufacturing so that control circuitry 42 is able to place display 14 and optical system 20 in a low-eye-strain configuration during normal operation. When calibrating device 10, device 10 can be tested to determine the position of display 40 that corresponds to a virtual image at infinity focus. This calibration information may then be stored in control circuitry 42.

If a user has perfect vision (no eye correction needed) and if device 10 is displaying distant content (e.g., content for which the user's vergence is associated with an object located at an infinite distance from the user), device 10 can adjust optical system 20 so that the extra diopter power of device 10 is zero. In this arrangement, the user will be able to comfortably view the distant content without eyestrain.

If, as another example, the user is nearsighted and typically needs a −1.00 diopter lens for comfortable viewing of distant images, control circuitry 42 can make a −1.00 diopter adjustment when distant images are presented and corresponding increased diopter changes as closer content is being presented.

If desired, eye characteristics can be sensed using a Tscherning sensor system or a ray tracing sensor system in addition to or instead of using a Shack-Hartmann sensor to measure refractive errors.

Figure 7A:
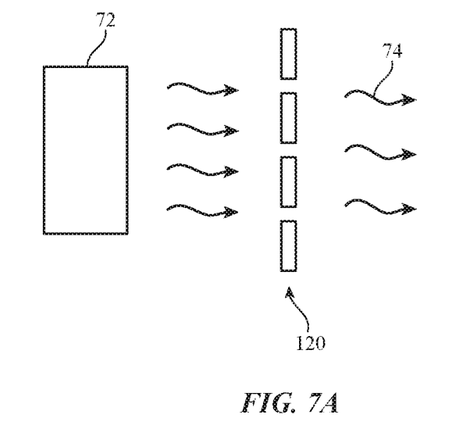
FIGS. 7A and 7B are diagrams of source and detector portions of a Tscherning sensor in accordance with an embodiment.
Figure 7B:
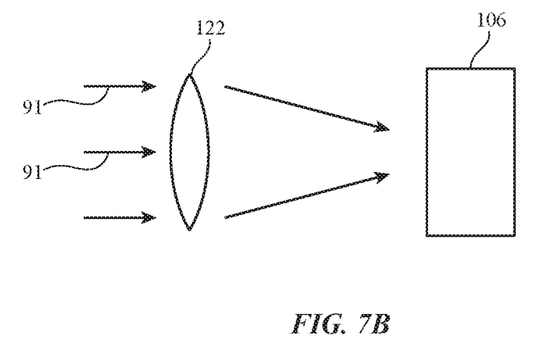

Portions of an illustrative Tscherning sensor system (Tscherning aberrometer) are shown in FIGS. 7A and 7B. In a Tscherning sensor system, collimated light 74 from a light source such as laser 72 or LED 73 is passed through a mask such as mask 120. Mask 120 has an array of openings such as an array of circular openings in a grid pattern having rows and columns. The presence of mask 120 converts light 74 into a series of parallel beams aligned with the array of openings in mask 120. These parallel beams are coupled into waveguide 84 and directed to eye 46 as light 88 as described in connection with FIG. 6A. After passing through eye 46 and forming images on the user's retina, these light beams return to waveguide 94 as light 90 (FIG. 6A). Waveguide 94 supplies light 90 to lens 122 as light 91, as shown in FIG. 7B. Camera 106 can measure the resulting array of spots of light associated with the reflected beams of light after light 91 passes through lens 122. Control circuitry 42 can analyze the measurements made by camera 106 to characterize refractive errors for the user's eye (e.g., using Zernike polynomials).

If desired, light source 72, mask 120, and waveguide 84 may be omitted and the array of light beams that would otherwise be passing through mask 120 may be generated instead by presenting an array of spots on display 40. Just prior to sensing the user's eyes, the user's eyes may be placed in a relaxed condition by forming an image on display 40 and moving this virtual target to infinity (e.g., by slowly increasing the separation between display 40 and eyes 46 until the infinity focus position has been reached and/or by tuning lenses in system 20). In this type of scenario, the light spots in the array may pass from display 40 to eye 46 without being routed to eye 46 using waveguide 84. Reflected light 90 may be supplied (as light 91) to camera 106 for analysis by control circuitry 42 (e.g., Zernike polynomial fitting, etc.).

Figure 8A:
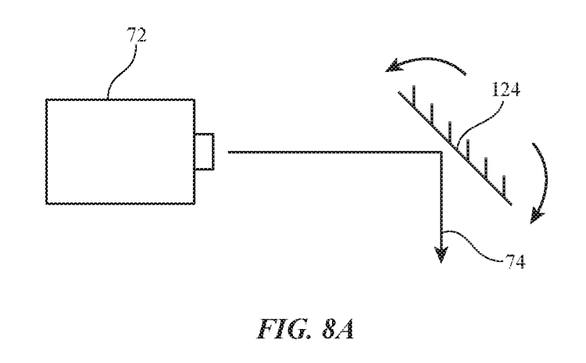
FIGS. 8A and 8B are diagrams of source and detector portions of a ray tracing sensor in accordance with an embodiment.
Figure 8B:
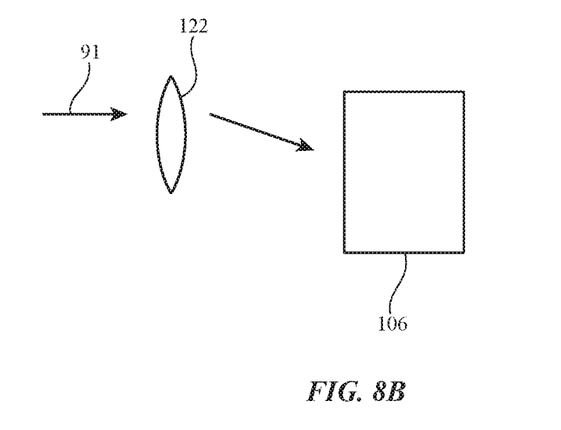

Portions of a ray tracing aberrometer are shown in FIGS. 8A and 8B. In a ray tracing system, a beam of light 74 from a light source such as laser 72 or LED 73 is scanned by an electrically controlled beam scanning device such as scanning mirror 124 (e.g., a mirror or other device controlled by control circuitry 42). The scanned beam is projected on the retina of eye 46 by waveguide 84 while the intensity of light 74 is pulsed by laser 72 or LED 73. This assembly forms an array of spots on the retina of eye 46. As each spot is projected onto eye 46 in sequence, reflected light for that spot (see, e.g., light 90 of FIG. 6A) is directed through waveguide 94 to lens 122 as light 91 of FIG. 8B. After passing through lens 122, camera 106 can capture an image of each of the spots and control circuitry 42 can analyze the captured image data (e.g., using Zernike polynomial fitting).

If desired, light for a ray-tracing sensing system (ray-tracing aberrometer) may be produced by forming patterns on display 40 after relaxing the user's eye 46. For example, a circle (ring of light) or other pattern may be formed on display 40. The user's eye 46 may be relaxed by moving the virtual target formed by the circle or other pattern to an infinity focus position before eye measurements are made. In this type of configuration, light source 72, mask 120, and waveguide 84 may be omitted. During measurements, the circular pattern of light on display 40 is directed onto the user's retina and reflected as reflected light 90. After passing through waveguide 94 in direction 96 and exiting as light 91, camera 106 can capture images of the circle (which may have the shape of an ellipse) for analysis by control circuitry 42. The magnification of the ellipse can be used in determining the spherical portion of the user's prescription, the major and minor axis of the ellipse can be used in determining the cylindrical portion of the user's prescription, and the axis of the user's prescription can be determined from the angle of the major axis of the ellipse measured with camera 106.

Figure 9:
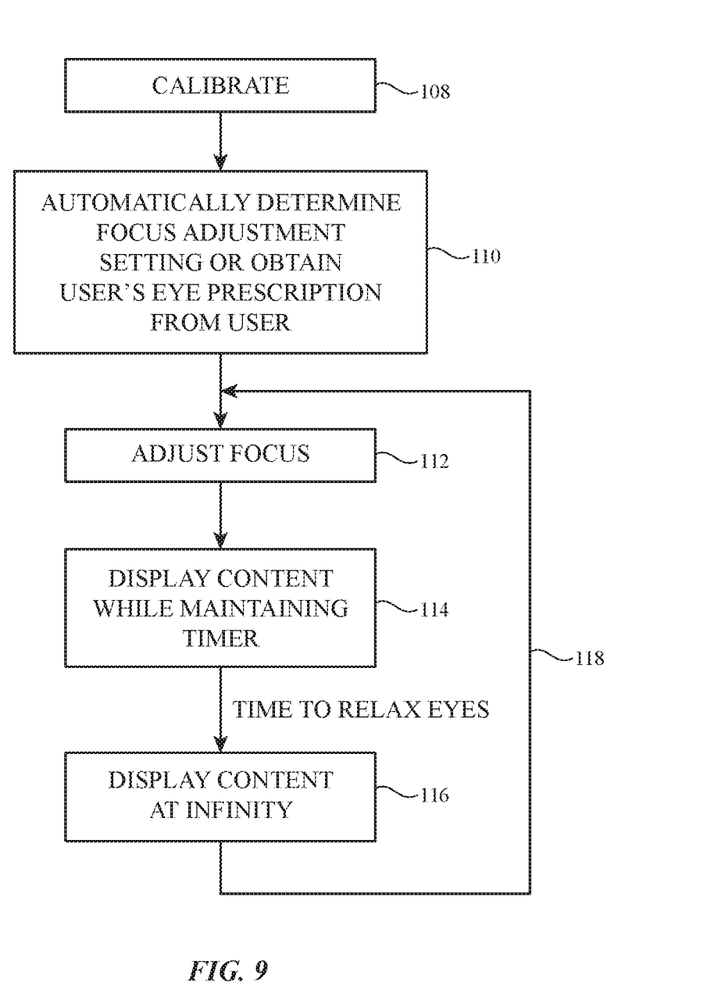
FIG. 9 is a flow chart of illustrative operations involved in operating a head-mounted device in accordance with an embodiment.

Illustrative operations involved in using device 10 are shown in FIG. 9.

During the operations of block 108, device 10 may be calibrated. For example, device 10 (or a representative device in a batch of devices being calibrated) can be characterized using test equipment. During testing, display 40 may create a test image while control circuitry 42 directs positioners in device 10 to position display 40 at its infinity focus location and directs lenses in lens system 20 to tune to their infinity focus location. An image sensor (e.g., a dummy eye) or other test sensor may be placed in the position of the user's eye while the image is displayed. Display position offsets and/or lens tuning offsets that might be needed to bring the virtual image at infinity into focus on the test sensor may then be determined and stored in device 10 to calibrated device 10 for future use by a user.

During user operations at block 110, device 10 may be adjusted (automatically and/or manually) so that lenses 20 and displays 40 are at appropriate locations relative to the user's eyes and face (e.g., so that lenses 20 and displays 40 are separated by an appropriate distance that matches the user's interpupillary distance, so that lenses 20 and displays 40 have appropriate Y locations, etc.). After these initial adjustments have been performed, device 10 may use an eye sensing system (e.g., an aberrometer such as a Hartmann-Shack, Tscherning, or ray tracing sensor or other suitable refractive error measurement equipment) to measure the characteristics of a user's eye (e.g., to automatically measure refractive errors for the user's eyes and therefore determine a user's eye prescription for both the user's left and right eyes). If desired, a user may manually supply information on the user's prescription to control circuitry 42 using input-output devices. A user may, for example, be prompted to supply prescription values (sphere, cylinder, axis) using a touch screen, keys, voice input, etc.

During the operations of block 112, control circuitry may adjust the position of display 40 (e.g., the separation in dimension Z of the left display from the user's left eye and the separation in dimension Z of the right display from the user's right eye) and/or may adjust tunable lenses in optical system 10 to bring content on display 40 into focus for the user while correcting for astigmatism, farsightedness, near-sightedness, and other refractive errors in the user's vision. The focus may be adjusted based on the nature of the content being displayed (e.g., based on the whether the content is distant content such as mountains in a landscape or is close-up content such as a nearby person) to minimize accommodation-vergence mismatch while taking into account user preferences and user refractive errors.

After the focus is adjusted at block 112, control circuitry 42 may use display system 40 to display images for the user. While displaying the images, control circuitry 42 can determine whether any of the content is associated with distant objects (distant virtual objects such as computer-generated distant mountains in a landscape) or is otherwise associated with the user's relaxed eye focus state (eyes focusing at infinity). A timer may be maintained to track the amount of time elapsed between periods in which long-distance (e.g., infinity focus) content is being displayed for more than a predetermined amount of time (e.g., at least 20 seconds, at least 10 seconds, a threshold amount of time less than 2 minutes, etc.).

When the timer expires (e.g., after at least 15 minutes, at least 20 minutes, 10-30 minutes, a time period of less than 40 minutes, or other suitable time limit beyond which the user is not allowed to continue without eye relaxation), control circuitry 42 can conclude that it is time for the user to relax their eyes. Accordingly, content at a large distance (e.g., at infinity or greater than 20 feet away) can be presented to the user (block 116). As the user views this distant content (and as control circuitry 42 adjust the position of display 40 and optical system 20 to their corresponding infinity focus states), the user's ciliary muscles in eyes 46 relax. After a suitable eye relaxation period has passed (e.g., after at least 10 s, at least 20 s, at least 30 s, at least 15-30 s, a time period less than 3 min, or other suitable relaxation time period), processing may return to block 112, as indicated by line 118. The eye relaxation content (long distance) content that is displayed during the operations of block 116 may include a message such as "relax eyes" that is presented at an infinity focus point or other suitably large distance or may include embedded content (e.g., mountains at an infinity focus or other suitable large distance) that is forced into the content that is otherwise being presented to the user. For example, a user playing a video game may be in a confined space and close to surrounding objects. To allow the user's eyes to relax during the operations of block 116, a distant mountain scene may be inserted into the video game, thereby avoiding the need to interrupt the user with a text message ("relax eyes") or other content that might disrupt the user's enjoyment of the video game.

A user of device 10 may not have perfect vision. For example, a user may be nearsighted, may be farsighted, and/or may have astigmatism. To correct for imperfect vision, vision correction lenses may be coupled to device 10. Lenses 20 may, for example, have a fixed portion and a removable vision correction portion.

Vision correction lenses may, for example, have a positive diopter (to correct for farsightedness or a negative diopter (to correct for nearsightedness). Astigmatism may also be corrected. Corrective lenses that correct for astigmatism are not be rotationally symmetric. To ensure that vision correction lenses that are not rotationally symmetric are oriented properly, device 10 may be provided with vision correction lens orientation features (e.g., a magnetic coupling structure or mechanical coupling structure that accurately aligns the corrective lens while coupling the corrective lens to lens 20L or 20R in device 10 so that the corrective lens has a desired angular orientation with respect to device 10 and display 40 and therefore to the user's eyes when device 10 is being worn by the user).

Figure 10:
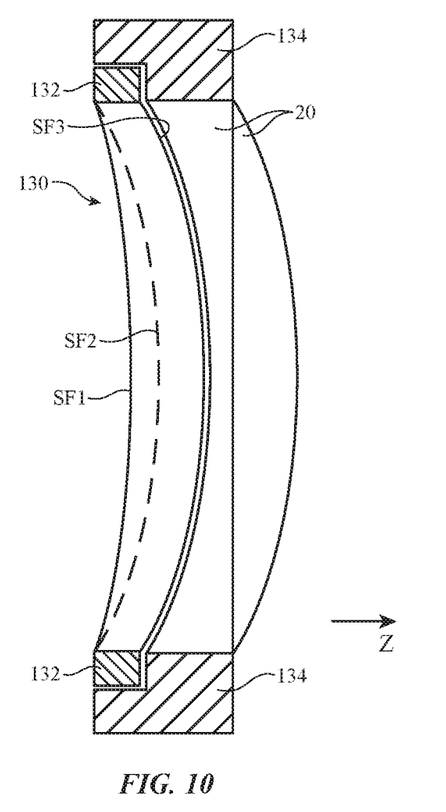
FIG. 10 is a side view of illustrative lens and an associated vision correction lens in accordance with an embodiment.

An illustrative vision correction lens arrangement is shown in FIG. 10. In the example of FIG. 10, vision correction lens 130 has been mounted within device 10 overlapping lens 20. Lens 20 may be a catadioptric lens or other suitable lens. Lens 20 may be tunable or may be fixed. Lens 130 may be rotationally symmetric or may be rotationally asymmetric. As shown in FIG. 10, lens 130 may have a convex outer surface SF3 that faces lens 20 and may have a concave inner surface. In configurations in which lens 130 is rotationally asymmetric to compensate for astigmatism, the concave inner surface of lens 130 may be characterized by a first curvature (shown by cross-sectional profile SF1) along a first dimension (e.g., along the X axis) and may be characterized by a different second curvature (shown by cross-sectional profile SF2) along a second dimension (e.g., along the Y axis). When lens 130 overlaps lens 20, a two-part lens is formed that is corrected to compensate for the user's vision problems.

Vision correction lens 130 may have a support structure such as vision correction lens mounting ring 132. Lens 20 may be mounted in a support structure such as lens mounting structure 134 (e.g., a portion of a housing or other structural support in device 10). Structure 134 may have an opening (e.g., a circular opening or an opening of other suitable shape) that receives mounting ring 132. When ring 132 is received within structure 134, alignment features associated with ring 132 and structure 134 accurately align vision correction ring 132 with respect to structure 134 (e.g., the angular orientation of ring 132 and therefore vision correction lens 130 with respect to lens 20, display 40, and other portions of device 10 is established within less than 2o, within less than 4o, or other suitable amount).

Figure 11:
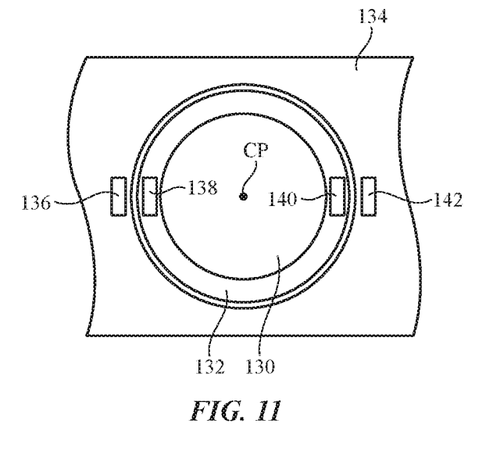
FIG. 11 is a front view of an illustrative vision correction lens coupled to a lens mount in accordance with an embodiment.

With one illustrative configuration, magnetic alignment structures may be used on ring 132 and structure 134. As shown in FIG. 11, for example, lens 130 may be mounted within ring 132 and may potentially rotate with respect to center point CP as ring 132 rotates within a circular opening in support structure 134. To place vision correction lens 130 into a desired rotational alignment with respect to structure 134 and the rest of device 10, ring 132 may be provided with one or more magnets such as magnets 138 and 140 and structure 134 may be provided with one or more corresponding magnets 136 and 142. When vision correction lens 130 is mounted to device 10, magnetic attraction between magnet 138 and magnet 136 and magnetic attraction between magnet 140 and 142 will help align and hold lens 130 in a desired angular orientation within device 10, thereby ensuring that lens 130 satisfactorily corrects a user's astigmatism.

Figure 12:
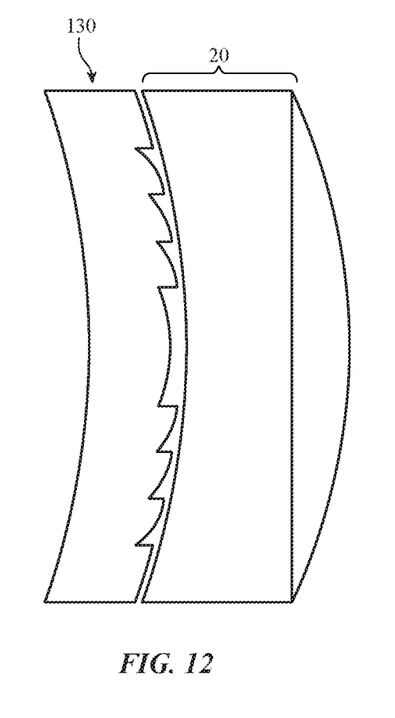
FIG. 12 is a side view of an illustrative lens and associated Fresnel vision correction lens in accordance with an embodiment.
Figure 13:
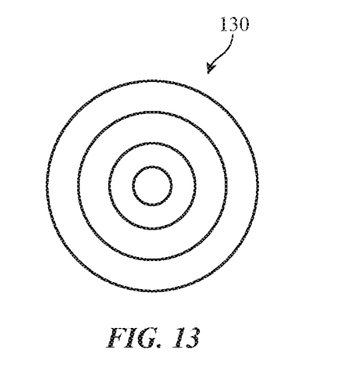
FIG. 13 is a front view of an illustrative spherical Fresnel lens in accordance with an embodiment.
Figure 14:
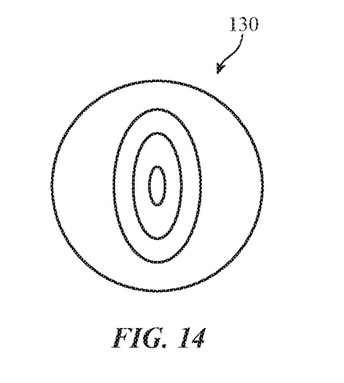
FIG. 14 is a front view of an illustrative cylindrical Fresnel lens in accordance with an embodiment.

If desired, vision correction lens 130 may be a Fresnel lens, as shown in FIG. 12. Fresnel vision correction lens 130 (e.g., lens 130 of FIG. 12) may be a spherical lens (e.g., a rotationally symmetric lens) as shown in the front view of lens 130 of FIG. 13 or may be a cylindrical lens (e.g., a cylindrical lens with no spherical power or a hybrid cylindrical-spherical lens) as shown in the front view of illustrative rotationally asymmetric lens 130 of FIG. 14.

To ensure that a user's vision is corrected satisfactorily when using device 10, vision correction lenses 130 may be coupled to device 10 in alignment with lenses 20 before use of device 10. For example, a left vision correction lens may be coupled to device 10 in alignment with (overlapping) left lens 20L and a right vision correction lens may be coupled to device 10 in alignment with right lens 20R. Vision correction lenses 130 may be coupled to device 10 magnetically (e.g., using magnets and/or magnetic material), using threaded retention rings, using clips, using adhesive, and/or using other suitable mounting structures. In some configurations, vision correction lenses 130 are removably coupled to device 10 (e.g., so that a different user may replace the vision correction lenses 130 with a different set of vision correction lenses if desired).

When vision correction lenses 130 are incorporated into device 10, lenses 130 and 20 operate together. For example, lenses 20 may serve to provide most of the optical power used in bringing display 40 into focus, while lenses 130 may correct for user-specific vision problems such as astigmatism, etc. If desired, tunable lens structures may be used in combination with vision correction lenses 130 and/or other fixed lenses (e.g., catadioptric lenses, Fresnel lenses, etc.).

In accordance with an embodiment, a head-mounted device configured to generate images viewable by a user having an eye with refractive errors that is located at an eye position is provided that includes a display configured to display the images, a lens through which the images are viewable, a sensor, a positioner coupled to the display, and control circuitry configured to measure the refractive errors with the sensor and configured to adjust the positioner based on the measured refractive errors.

In accordance with another embodiment, the sensor includes at least one waveguide.

In accordance with another embodiment, the sensor includes an input coupler that couples light into the waveguide and includes an output coupler that couples light out of the waveguide.

In accordance with another embodiment, the output coupler is configured to allow images to pass from the display to the eye position.

In accordance with another embodiment, the input coupler and output coupler are volume holograms.

In accordance with another embodiment, the sensor further includes a camera that measures light from the output coupler.

In accordance with another embodiment, the head-mounted device includes a light source selected from the group consisting of a laser and a light emitting diode that supplies light, an additional waveguide having an additional input coupler that couples the light into the additional waveguide and that has an additional output coupler that directs the light out of the additional waveguide towards the eye position.

In accordance with another embodiment, the head-mounted device includes a lens array interposed between the output coupler and the camera, the control circuitry is configured to measure the refractive errors by analyzing light spots produced by the lens array at the camera.

In accordance with another embodiment, the sensor is configured to form a Shack-Hartmann aberrometer.

In accordance with another embodiment, the sensor is configured to form a Tscherning aberrometer and the control circuitry is configured to measure the refractive errors by analyzing light spots at the camera that are produced while an array of dots are displayed on the display.

In accordance with another embodiment, the sensor is configured to form a ray tracing aberrometer and the control circuitry is configured to measure the refractive errors by analyzing a light pattern at the camera that is produced while a shape is displayed on the display.

In accordance with another embodiment, the shape includes a circle.

In accordance with another embodiment, the control circuitry is configured to allow the eye to relax by periodically presenting content on the display while adjusting at least a selected one of: the display and the lens to an infinity focus setting.

In accordance with another embodiment, the head-mounted device includes an input-output device, the control circuitry is configured to receive user input on the refractive errors with the input-output device.

In accordance with another embodiment, the user input includes an eyeglasses prescription and the control circuitry is configured to adjust a position of the display with the positioner based on the eyeglasses prescription.

In accordance with another embodiment, the lens includes a tunable lens and the control circuitry is configured to adjust the tunable lens based at least partly on the measured refractive errors.

In accordance with another embodiment, the tunable lens includes at least one tunable liquid crystal cylindrical lens, the measured refractive errors are associated with astigmatism in the eye, and the control circuitry is configured to adjust the tunable liquid crystal cylindrical lens based on the measured refractive errors to correct the astigmatism.

In accordance with another embodiment, the lens includes a vision correction lens.

In accordance with another embodiment, the vision correction lens is rotationally asymmetric and is configured to compensate for astigmatism.

In accordance with another embodiment, the vision correction lens is a Fresnel lens.

In accordance with another embodiment, the lens includes a fixed lens and a removable vision correction lens that is configured to overlap the fixed lens.

In accordance with another embodiment, the removable vision correction lens includes rotational alignment structures configured to rotationally align the removable vision correction lens relative to the fixed lens.

In accordance with another embodiment, the rotational alignment structures include a magnet.

In accordance with an embodiment, a head-mounted device is provided that includes a display configured to display images, a lens, a sensor that includes at least one hologram, and control circuitry configured to measure refractive errors in eyes with the sensor and configured to adjust at least one of: the lens and a position of the display based on the measured refractive errors.

In accordance with another embodiment, the sensor includes a camera, the refractive errors includes astigmatism, the lens includes an adjustable liquid crystal cylindrical lens, and the control circuitry is configured to adjust the adjustable liquid crystal cylindrical lens to correct the astigmatism as the display is viewed.

In accordance with an embodiment, a head-mounted device is provided that includes a display, a lens through which the display is viewable from an eye position, a waveguide, a hologram on the waveguide through which the display is viewable from the eye position, a camera, and control circuitry configured to measure eye refractive errors based on measurements with the camera on light exiting the waveguide.

The foregoing is merely illustrative and various modifications can be made to the described embodiments. The foregoing embodiments may be implemented individually or in any combination.

What is claimed is:

1. A head-mounted device configured to generate images viewable by a user having an eye with refractive errors that is located at an eye position, comprising:
   a display configured to display the images;
   a lens through which the images are viewable;
   a sensor having a waveguide configured to receive light from a light source and to provide the received light towards the eye position and having a camera configured to receive a reflected version of the light from the eye position, wherein the waveguide, the lens, and the display overlap the eye position along a same direction in front of the eye position;
   a positioner coupled to the display; and
   control circuitry configured to measure the refractive errors with the sensor and configured to adjust the positioner based on the measured refractive errors.

2. The head-mounted device defined in claim 1, wherein the sensor includes an additional waveguide that overlaps the eye position.

3. The head-mounted device defined in claim 2, wherein the sensor includes an input coupler that couples the reflected version of the light into the additional waveguide and includes an output coupler that couples the reflected version of the light out of the additional waveguide.

4. The head-mounted device defined in claim 3, wherein the input coupler is configured to allow the images to pass from the display to the eye position.

5. The head-mounted device defined in claim 4, wherein the input coupler and the output coupler are volume holograms.

6. The head-mounted device defined in claim 5, wherein the camera measures the reflected version of the light from the output coupler.

7. The head-mounted device defined in claim 6, wherein the waveguide has an additional input coupler that couples the light into the waveguide and that has an additional output coupler that directs the light out of the waveguide towards the eye position, wherein the light source is selected from the group consisting of: a laser and a light emitting diode.

8. The head-mounted device defined in claim 7, further comprising a lens array interposed between the output coupler and the camera, wherein the control circuitry is configured to measure the refractive errors by analyzing light spots produced by the lens array at the camera.

9. The head-mounted device defined in claim 8, wherein the sensor is configured to form a Shack-Hartmann aberrometer.

10. The head-mounted device defined in claim 6, wherein the sensor is configured to form a Tscherning aberrometer and wherein the control circuitry is configured to measure the refractive errors by analyzing light spots at the camera that are produced while an array of dots are provided to the eye position.

11. The head-mounted device defined in claim 6, wherein the sensor is configured to form a ray tracing aberrometer and wherein the control circuitry is configured to measure the refractive errors by analyzing a light pattern at the camera that is produced while a shape is provided to the eye position.

12. The head-mounted device defined in claim 1, wherein the control circuitry is configured to allow the eye to relax by periodically presenting content on the display while adjusting at least a selected one of: the display and the lens to an infinity focus setting.

13. The head-mounted device defined in claim 1, further comprising an input-output device, wherein the control circuitry is configured to receive user input on the refractive errors with the input-output device.

14. The head-mounted device defined in claim 13, wherein the user input comprises an eyeglasses prescription and wherein the control circuitry is configured to adjust a position of the display with the positioner based on the eyeglasses prescription.

15. The head-mounted device defined in claim 1, wherein the lens comprises a tunable lens and wherein the control circuitry is configured to adjust the tunable lens based at least partly on the measured refractive errors.

16. The head-mounted device defined in claim 15, wherein the tunable lens comprises at least one tunable liquid crystal cylindrical lens, wherein the measured refractive errors are associated with astigmatism in the eye, and wherein the control circuitry is configured to adjust the tunable liquid crystal cylindrical lens based on the measured refractive errors to correct the astigmatism.

17. The head-mounted device defined in claim 1, wherein the lens includes a vision correction lens.

18. The head-mounted device defined in claim 17, wherein the vision correction lens is rotationally asymmetric and is configured to compensate for astigmatism.

19. The head-mounted device defined in claim 17, wherein the vision correction lens is a Fresnel lens.

20. The head-mounted device defined in claim 1, wherein the lens includes a fixed lens and a removable vision correction lens that is configured to overlap the fixed lens.

21. The head-mounted device defined in claim 20, wherein the removable vision correction lens comprises rotational alignment structures configured to rotationally align the removable vision correction lens relative to the fixed lens.

22. A head-mounted device, comprising:
a display configured to display images;
a lens;
a sensor that includes a light source configured to produce light, a waveguide configured to receive the light produced by the light source via an input coupler, and an output coupler configured to couple the received light out of the waveguide towards an eye position, wherein the display and the output coupler overlap the eye position in a same direction in front of the eye position; and
control circuitry configured to measure refractive errors in eyes with the sensor based on the light coupled out of the waveguide and configured to adjust at least one of: the lens and a position of the display based on the measured refractive errors.

23. The head-mounted device defined in claim 22, wherein the sensor includes a camera, wherein the refractive errors include astigmatism, wherein the lens comprises an adjustable liquid crystal cylindrical lens, and wherein the control circuitry is configured to adjust the adjustable liquid crystal cylindrical lens to correct the astigmatism as the display is viewed.

24. The head-mounted device defined in claim 22 wherein the lens overlaps the eye position along the same direction in front of the eye position.

25. A head-mounted device, comprising:
a display;
a lens through which the display is viewable from an eye position;
a waveguide;
an input coupler on the waveguide through which the display is viewable from the eye position, wherein the input coupler, the lens, and the display overlap the eye position along a same direction in front of the eye position;
a camera; and
control circuitry configured to measure eye refractive errors based on measurements with the camera on light exiting the waveguide.

26. The head-mounted device defined in claim 25, further comprising:
an output coupler on the waveguide configured to couple the light out of the waveguide towards the camera.

* * * * *